(12) United States Patent
Greer et al.

(10) Patent No.: US 10,932,671 B2
(45) Date of Patent: Mar. 2, 2021

(54) LIVESTOCK HEALTH MONITORING SYSTEM AND METHOD OF USE

(71) Applicant: FEVERTAGS LLC, Amarillo, TX (US)

(72) Inventors: John M. Greer, Dallas, TX (US); Richard Arelin Crider, Jr., Dripping Springs, TX (US); Alvin Cecil Fults, Amarillo, TX (US)

(73) Assignee: FEVERTAGS, LLC, Amarillo, TX (US)

( * ) Notice: Subject to any disclaimer, the term of this patent is extended or adjusted under 35 U.S.C. 154(b) by 0 days.

(21) Appl. No.: 16/544,685

(22) Filed: Aug. 19, 2019

(65) Prior Publication Data

US 2020/0037886 A1 Feb. 6, 2020

Related U.S. Application Data

(63) Continuation-in-part of application No. 16/439,518, filed on Jun. 12, 2019, now Pat. No. 10,813,558, and
(Continued)

(51) Int. Cl.
*A61B 5/01* (2006.01)
*A01K 11/00* (2006.01)
(Continued)

(52) U.S. Cl.
CPC ............... *A61B 5/01* (2013.01); *A01K 11/00* (2013.01); *A01K 11/001* (2013.01);
(Continued)

(58) Field of Classification Search
CPC ....... A61B 5/01; A61B 5/6816; A61B 5/6817; A61B 5/0008; A61B 5/0022;
(Continued)

(56) References Cited

U.S. PATENT DOCUMENTS 5,725,308 A * 3/1998 Smith ................ G01K 7/42
374/169
9,370,170 B2 * 6/2016 Downing ............. A01K 11/006
(Continued)

FOREIGN PATENT DOCUMENTS

KR 2020060000192 U 12/2006
KR 101213252 B1 12/2012
KR 1020180112972 A 10/2018

OTHER PUBLICATIONS

Korean Patent Office, Written Opinion issued in PCT/US2020/046776, dated Nov. 25, 2020, 7 pages.
(Continued)

*Primary Examiner* — Mohammad K Islam
(74) *Attorney, Agent, or Firm* — Jerry C. Harris, Jr.

(57) ABSTRACT

An animal wellness notification system includes an attachment body configured to securely engage with an ear of the animal; an elongated temperature probe secured to the attachment body and configured to extend within the ear of the animal; a housing secured to the attachment body; a power module electrically connect to and configured to provide power to (or recharge) at least one other element of the animal wellness notification system; a computer disposed within the housing and operably associated with the temperature probe; and a notification device in data communication with the computer, the notification device being configured to provide notice if a temperature of the animal goes beyond a determined threshold.

20 Claims, 13 Drawing Sheets

Related U.S. Application Data a continuation-in-part of application No. PCT/US2017/019464, filed on Feb. 24, 2017, and a continuation of application No. 15/440,793, filed on Feb. 23, 2017, now Pat. No. 10,398,317, and a continuation of application No. 15/440,793, filed on Feb. 23, 2017, now Pat. No. 10,398,317, and a continuation-in-part of application No. 14/879,407, filed on Oct. 9, 2015, now Pat. No. 10,687,515, and a continuation-in-part of application No. 14/879,407, filed on Oct. 9, 2015, now Pat. No. 10,687,515.

(60) Provisional application No. 62/337,400, filed on May 17, 2016, provisional application No. 62/102,416, filed on Jan. 12, 2015.

(51) Int. Cl.
| | | |
|---|---|---|
| *A61B 5/00* | (2006.01) | |
| *G01K 1/02* | (2021.01) | |
| *G01K 3/00* | (2006.01) | |
| *G01K 13/00* | (2021.01) | |
| *A01K 29/00* | (2006.01) | |
| *G08B 21/18* | (2006.01) | |
| *G01K 1/024* | (2021.01) | |

(52) U.S. Cl.
CPC .......... *A01K 11/004* (2013.01); *A01K 29/005* (2013.01); *A61B 5/0008* (2013.01); *A61B 5/0022* (2013.01); *A61B 5/6816* (2013.01); *A61B 5/6817* (2013.01); *A61B 5/742* (2013.01); *A61B 5/7405* (2013.01); *G01K 1/024* (2013.01); *G01K 3/005* (2013.01); *G01K 13/002* (2013.01); *G08B 21/182* (2013.01); *A61B 2503/40* (2013.01)

(58) Field of Classification Search
CPC ... A61B 5/7405; A61B 5/742; A61B 2503/40; A61B 5/746; G01K 1/024; G01K 3/005; G01K 13/002; G08B 21/182; A01K 11/001; A01K 11/004; A01K 11/00; A01K 29/005

See application file for complete search history.

(56) References Cited

U.S. PATENT DOCUMENTS

| | | | |
|---|---|---|---|
| 9,504,387 B2* | 11/2016 | Alonsoperez Lanza | G06F 19/00 |
| 9,848,577 B1* | 12/2017 | Brandao | A01K 11/006 |
| 10,039,267 B1 | 8/2018 | Thiex et al. | |
| 2004/0233971 A1* | 11/2004 | Meads | G01K 1/026 374/208 |
| 2014/0333439 A1* | 11/2014 | Downing | A01K 29/005 340/573.3 |
| 2015/0334990 A1* | 11/2015 | Nir | A61B 5/0077 600/301 |
| 2016/0073968 A1* | 3/2016 | Koyama | A61B 5/0537 600/301 |
| 2016/0165851 A1* | 6/2016 | Harty | A61B 5/7282 600/595 |
| 2018/0235184 A1 | 8/2018 | Harty et al. | |

OTHER PUBLICATIONS

Korean Patent Office, International Search Report issued in PCT/US2020/046776, dated Nov. 27, 2020, 3 pages.

* cited by examiner

LIVESTOCK HEALTH MONITORING SYSTEM AND METHOD OF USE

CROSS-REFERENCE TO RELATED APPLICATIONS

This application is a continuation-in-part, and claims priority to, U.S. patent application Ser. No. 16/439,518 filed on Jun. 12, 2019 and entitled "Livestock Health Monitoring System and Method of Use," which is a continuation of, and claims priority to, U.S. patent application Ser. No. 15/440,793 filed on Feb. 23, 2017 and entitled "Livestock Health Monitoring System and Method of Use," which claims priority to U.S. Provisional Patent Application Ser. No. 62/337,400 filed on May 17, 2016 and entitled "Livestock Health Monitoring System and Method of Use"; U.S. patent application Ser. No. 15/440,793 is also a continuation-in-part of U.S. patent application Ser. No. 14/879,407 filed on Oct. 9, 2015 and entitled "Livestock Health Monitoring System Having Elongated Temperature Probe for the Ear and Method of Use," which claims priority to U.S. Provisional Patent Application Ser. No. 62/102,416 filed on Jan. 12, 2015 and entitled "Electrical Mechanical Device Used to Detect and Alarm Health Status of Bovine."

This application is also a continuation-in-part, and claims priority as a bypass application to, International Patent Application No. PCT/US2017/019464 filed on Feb. 24, 2017 and entitled "Livestock Health Monitoring System and Method of Use," which is an international application based on, and claims priority to, U.S. patent application Ser. No. 15/440,793 filed on Feb. 23, 2017 and entitled "Livestock Health Monitoring System and Method of Use," which claims priority to U.S. Provisional Patent Application Ser. No. 62/337,400 filed on May 17, 2016 and entitled "Livestock Health Monitoring System and Method of Use"; U.S. patent application Ser. No. 15/440,793 is also a continuation-in-part of U.S. patent application Ser. No. 14/879,407 filed on Oct. 9, 2015 and entitled "Livestock Health Monitoring System Having Elongated Temperature Probe for the Ear and Method of Use," which claims priority to U.S. Provisional Patent Application Ser. No. 62/102,416 filed on Jan. 12, 2015 and entitled "Electrical Mechanical Device Used to Detect and Alarm Health Status of Bovine."

This application is also a continuation-in-part of U.S. patent application Ser. No. 14/879,407 filed on Oct. 9, 2015 and entitled "Livestock Health Monitoring System Having Elongated Temperature Probe for the Ear and Method of Use," which claims priority to U.S. Provisional Patent Application Ser. No. 62/102,416 filed on Jan. 12, 2015 and entitled "Electrical Mechanical Device Used to Detect and Alarm Health Status of Bovine."

BACKGROUND

The present disclosure relates generally to systems and methods to determine the health of livestock, and embodiments of the disclosure include a livestock health monitoring system for data collection and detection of abnormal health conditions.

Systems and methods to determine the health of livestock are well known in the art and are effective means to detect illness and implement treatment in livestock. For example, a conventional livestock monitoring system may have a livestock manager overseeing a plurality of livestock and may be in communication with a veterinarian. The livestock manager monitors livestock via visual inspection. When unusual behavior of the livestock occurs, as indicative of illness, the livestock manager contacts a veterinarian, who then makes a prognosis and begins treatment.

One of the problems commonly associated with the above described monitoring system is insufficient monitoring and/or inexperience of the livestock manager. For example, the process of monitoring could involve a large number of livestock, making the monitoring process difficult. In addition, the process suffers a substantial risk of human error, as many livestock illnesses are visually undetectable and/or the livestock manager fails to adequately determine whether the livestock is ill. Accordingly, although great strides have been made in the area of system and methods to determine livestock wellness, many shortcomings remain.

BRIEF DESCRIPTION OF THE DRAWINGS

The novel features believed characteristic of the embodiments of the present application are set forth in the appended claims. However, the embodiments themselves and further objectives and advantages thereof, will best be understood by reference to the following detailed description when read in conjunction with the accompanying drawings, wherein:

Figure 1:
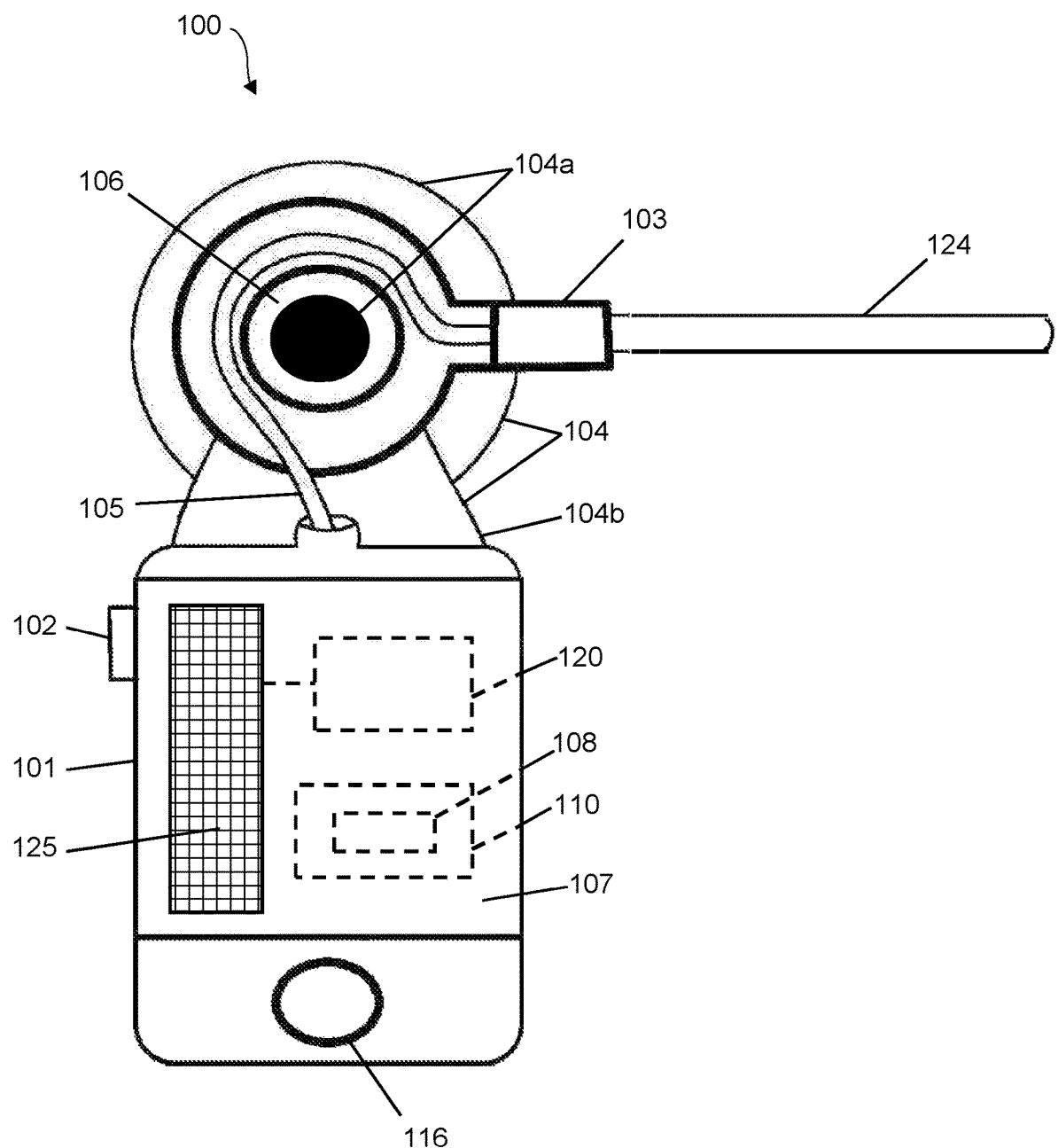
FIG. 1 illustrates a front view of a livestock health monitoring system according to an embodiment of the disclosure.

While the system and method of use of the present application is susceptible to various modifications and alternative forms, specific embodiments thereof have been shown by way of example in the drawings and are herein described in detail. It should be understood, however, that the description herein of specific embodiments is not intended to limit the invention to the particular embodiment disclosed, but on the contrary, the intention is to cover all modifications, equivalents, and alternatives falling within the spirit and scope of the present application as defined by the appended claims.

DETAILED DESCRIPTION

Illustrative embodiments of the system and method of use of the present disclosure are provided below. It will of course be appreciated that in the development of any actual embodiment, numerous implementation-specific decisions will be made to achieve the developer's specific goals, such as compliance with system-related and business-related constraints, which will vary from one implementation to another. Moreover, it will be appreciated that such a development effort might be complex and time-consuming but would nevertheless be a routine undertaking for those of ordinary skill in the art having the benefit of this disclosure.

The system and method of use in accordance with the present application overcomes problems commonly associated with conventional livestock monitoring systems. Specifically, the present invention provides a rapid and effective means to monitor large numbers of livestock and reduces the risk of human error. Additionally, systems of the disclosure may allow for longer term monitoring provided by rechargeable monitoring devices. These and other unique features of the system and method of use are discussed below and illustrated in the accompanying drawings.

The system and method of use will be understood, both as to its structure and operation, from the accompanying drawings, taken in conjunction with the accompanying description. Several embodiments of the system are presented herein. It should be understood that various components, parts, and features of the different embodiments may be combined together and/or interchanged with one another, all of which are within the scope of the present application, even though not all variations and particular embodiments are shown in the drawings. It should also be understood that the mixing and matching of features, elements, and/or functions between various embodiments is expressly contemplated herein so that one of ordinary skill in the art would appreciate from this disclosure that the features, elements, and/or functions of one embodiment may be incorporated into another embodiment as appropriate, unless described otherwise.

Figure 3:
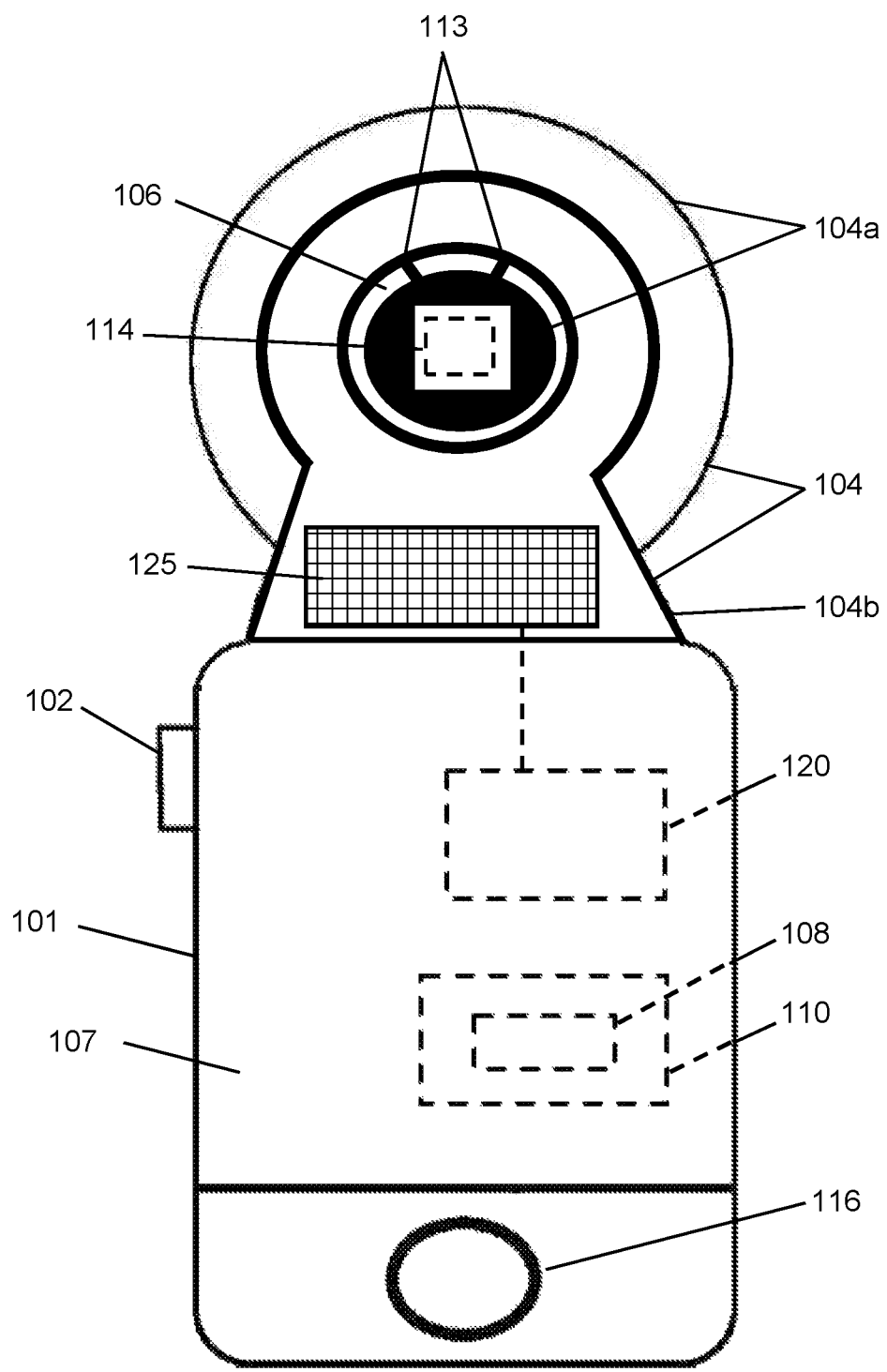
FIG. 3 illustrates a front view of a heath monitoring device according to an embodiment of the disclosure.
Figure 8:
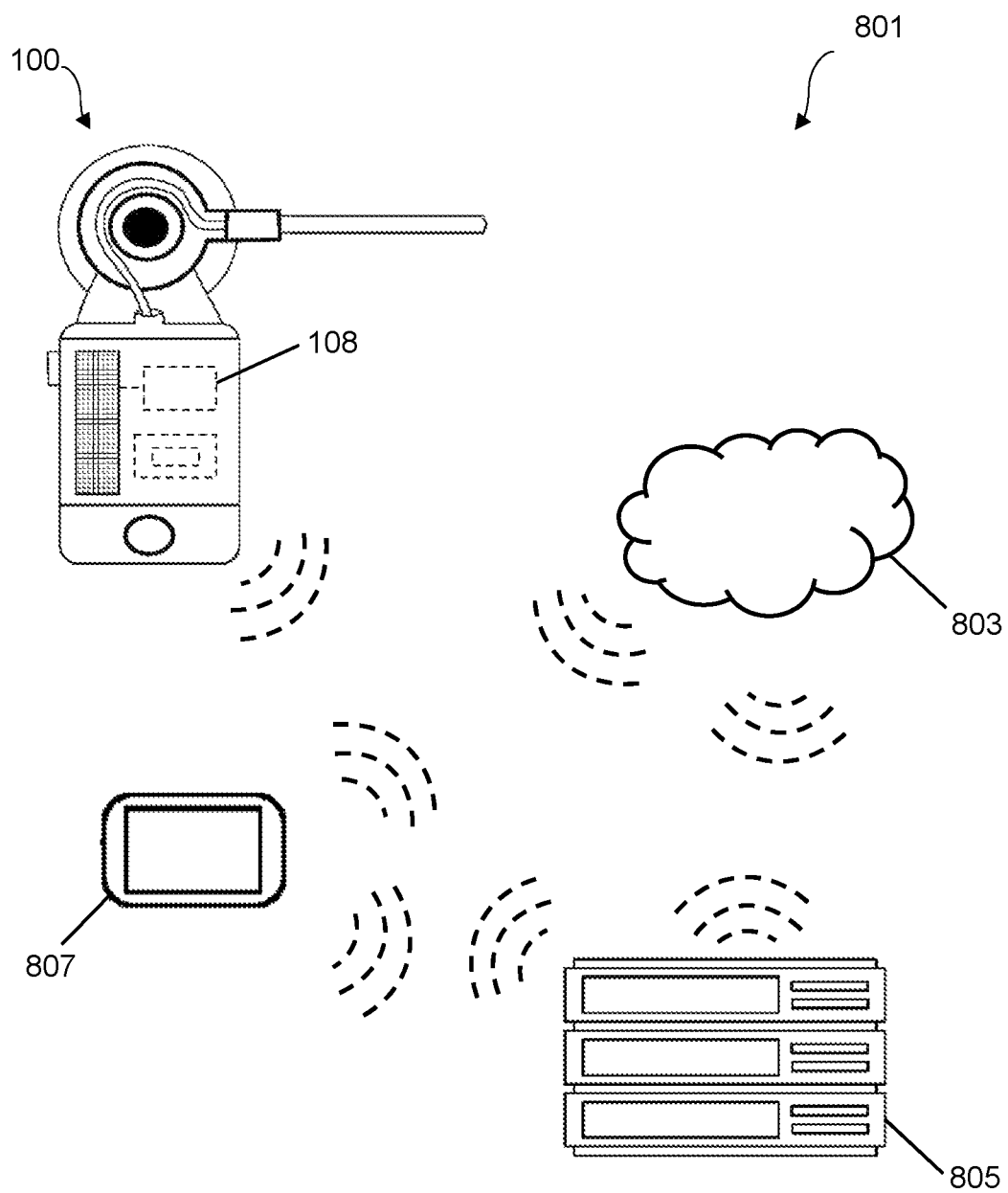
FIG. 8 illustrates a communication system according to an embodiment of the disclosure.

Referring now to the drawings wherein like reference characters identify corresponding or similar elements throughout the several views, FIG. 8 depicts a front view of a livestock health monitoring system 801. In the embodiment shown in FIGS. 5 and 6, the monitoring system 601 includes a health monitoring device 100 comprising a temperature monitoring component (e.g., a temperature probe 124 and/or temperature sensor 114) in communication with an animal 603 via an attachment body 104. During use, the attachment body 104 is secured to the ear 605 of the animal 603 via one or more types of fasteners commonly known in the art. For example, as shown in FIG. 3, the attachment body 104 may include a body having a hole 106 extending therethrough. The fastener is secured to the hole 106, which in turn is secured to the ear 605.

Figure 2:
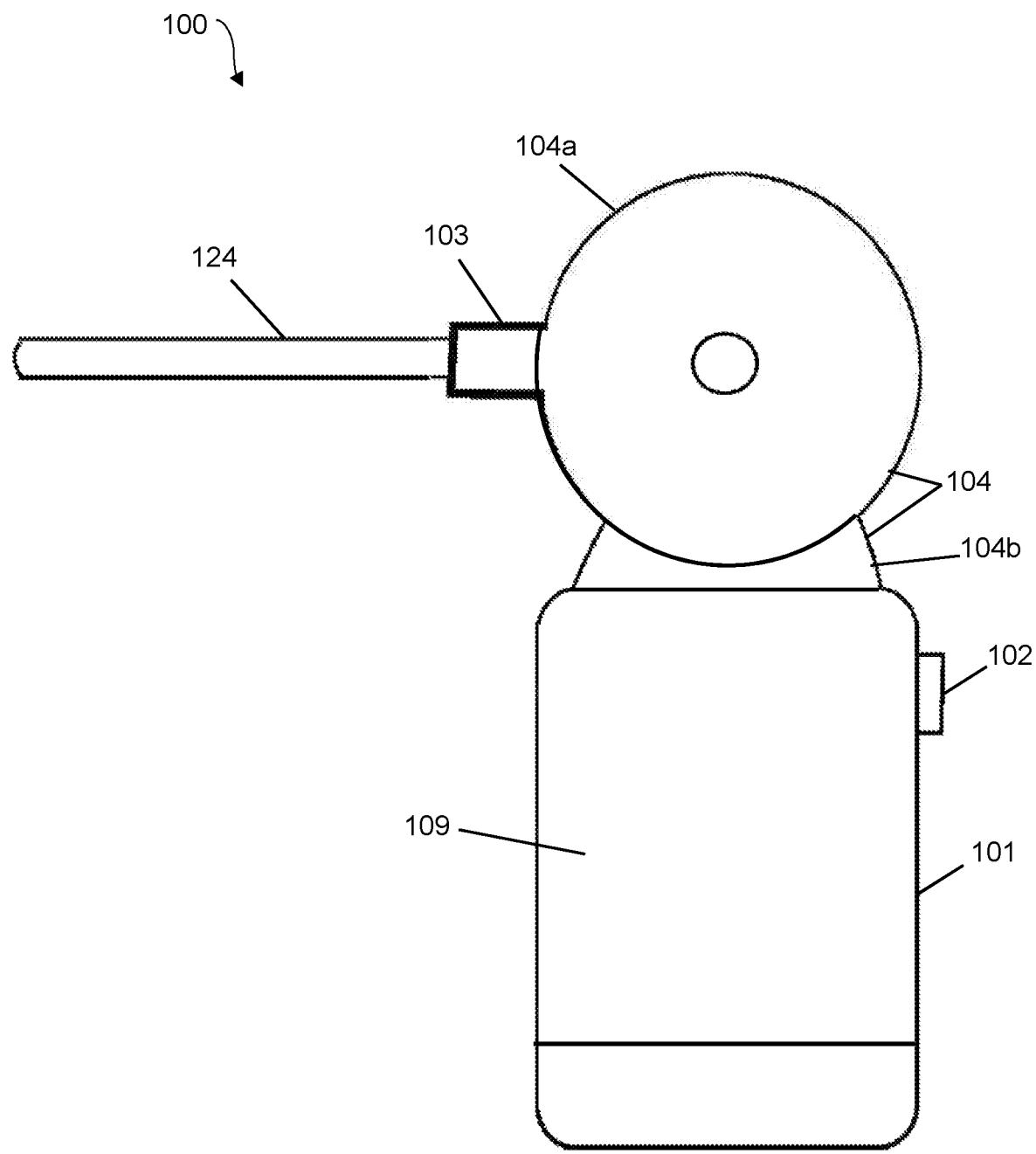
FIG. 2 illustrates a back view of a heath monitoring device according to an embodiment of the disclosure.

As shown in FIGS. 1 and 2, the health monitoring device 100 comprises a data collection housing 101 comprising an on/off switch 102 (e.g., a depression switch), a rotational device 103 which is rotatably connected to attachment body 104 (e.g., rotatably connected to male portion 104a, female portion 104b, or both male portion 104a and female portion 104b), and a temperature probe 124. The data collection housing 101 may attached to the attachment body 104 and be in communication with a rotational device 103 and a temperature probe 124 via a wire 105. In an embodiment, the elongated temperature probe 124 is positioned through the rotational device 103 and the elongated temperature probe 124 may comprise a material capable of changing hardness upon reaching a particular temperature. In some embodiments, the data collection housing 101 may comprise a notification device 116 and may be enclosed in weather resistant material. In an embodiment, the notification device 116 may comprise a visual alert, an audible alert, and/or a wireless alert that is communicated to another device. For example, the notification device 116 may comprise a light that can be visually seen by a worker, an audible speaker, and/or a transmitter configured to provide notification to a remote device (for example, as depicted in FIG. 8).

Figure 4A:
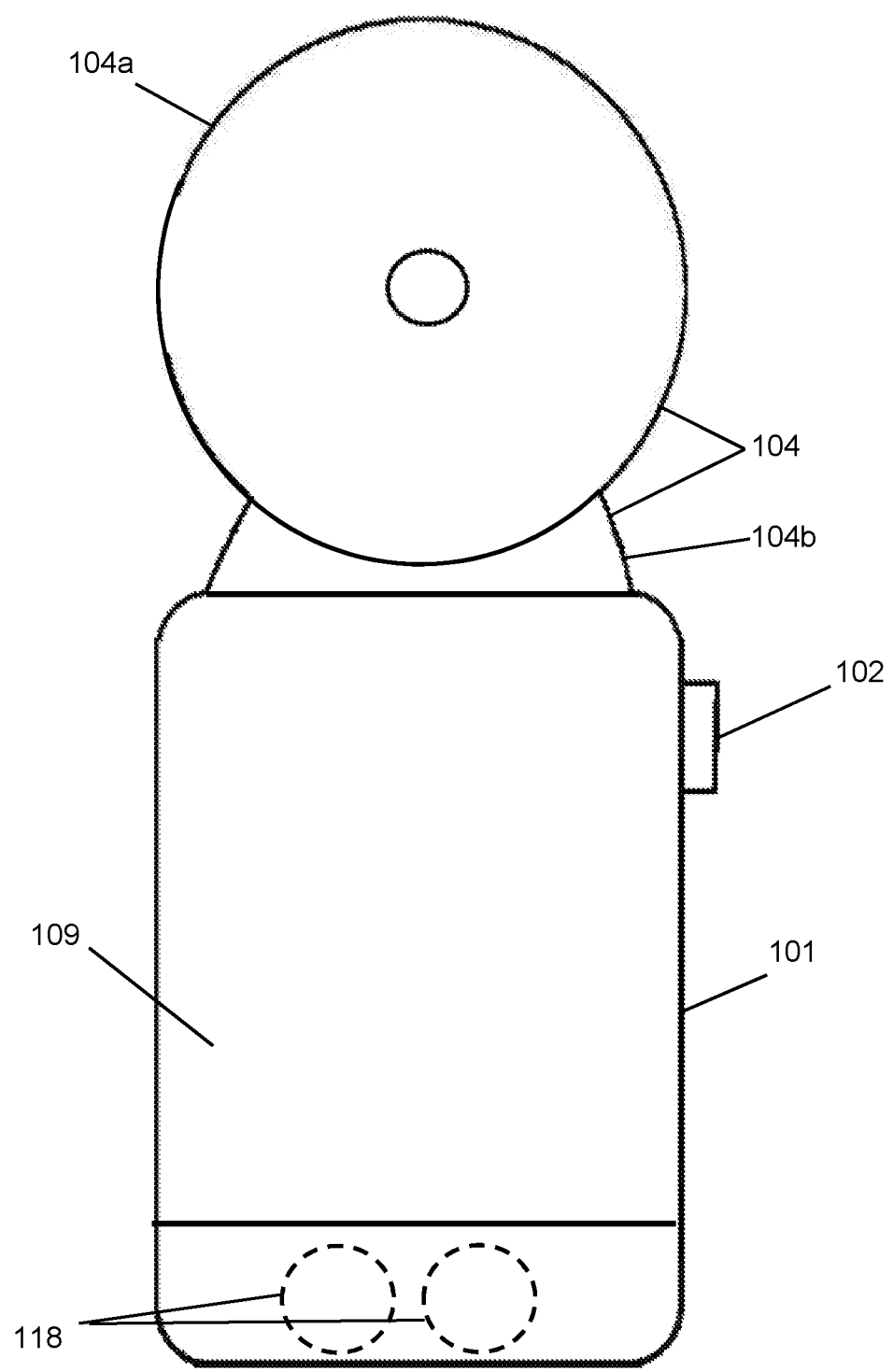
FIG. 4A illustrates a back view of a heath monitoring device according to an embodiment of the disclosure.
Figure 4B:
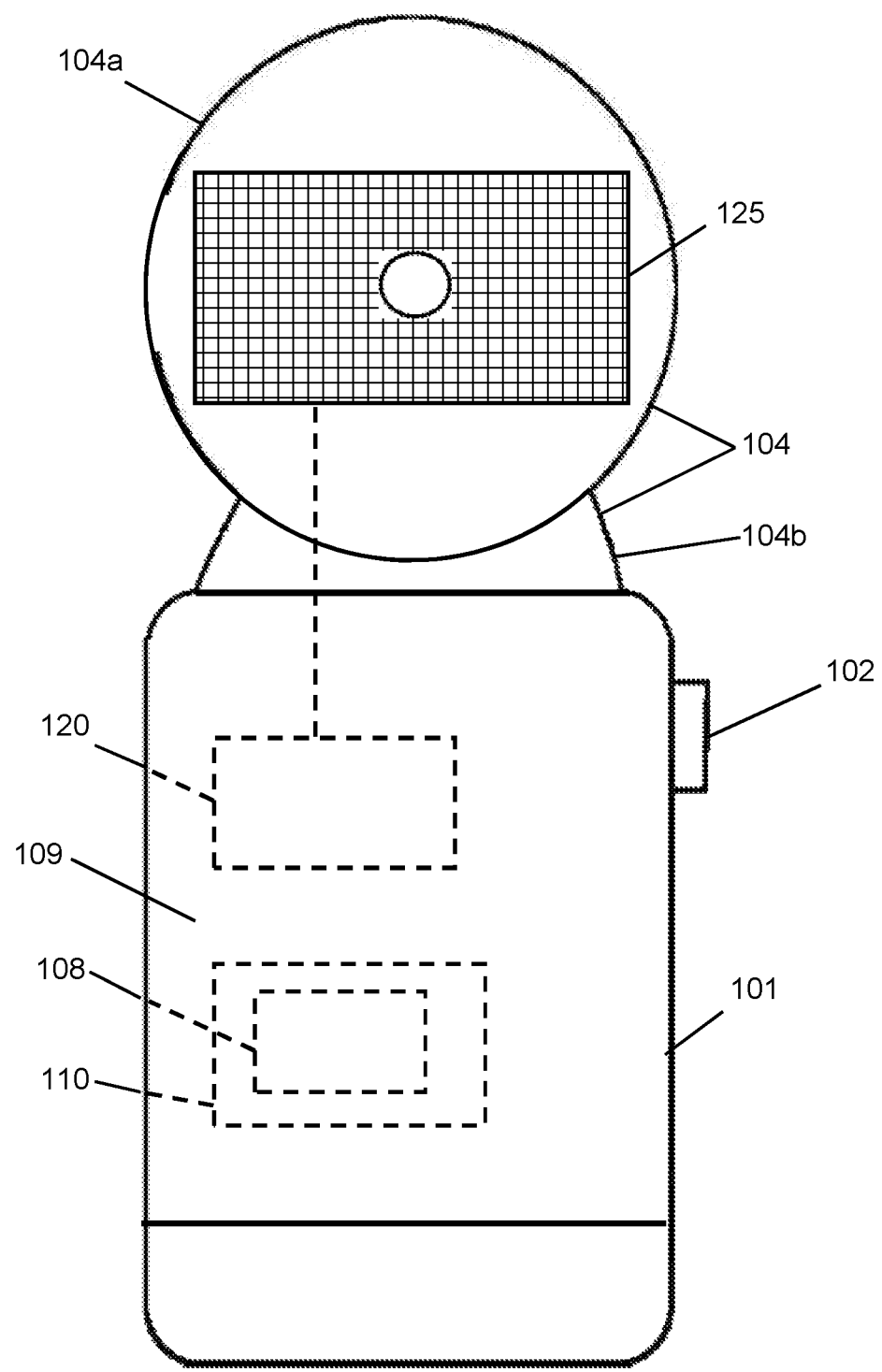
FIG. 4B illustrates a back view of a heath monitoring device according to an embodiment of the disclosure.

As shown in FIGS. 3 and 4A-4B, the health monitoring device 100 comprises a data collection housing 101 comprising an on/off switch 102 (e.g., a depression switch). The data collection housing 101 may attached to the attachment body 104 and be in communication with a temperature sensor 114 via a wire 105. In an embodiment, the temperature sensor 114 is comprised in a male portion 104a of attachment body 104. In an embodiment, the temperature sensor 114 is comprised in a female portion 104b of attachment body 104. In an embodiment, the temperature sensor 114 is comprised in a male portion 104a and a female portion 104b of attachment body 104. In some embodiments, the data collection housing 101 may comprise a notification device 116 and may be enclosed in weather resistant material. In an embodiment, the notification device 116 may comprise a visual alert, an audible alert, and/or a wireless alert that is communicated to another device. For example, the notification device 116 may comprise a light that can be visually seen by a worker, an audible speaker, and/or a transmitter configured to provide notification to a remote device (for example, as depicted in FIG. 8).

A health monitoring computer 110 may be positioned within housing 101, wherein the health monitoring computer 110 may comprise software, hardware, and power supply configured to determine if a temperature threshold is reached and/or to activate the notification device 116. The health monitoring computer 110 may receive information from the temperature probe 124 via the wire 105. The computer system may also comprise a wireless communication module configured to wirelessly communicate information to and/or from a remote device (for example, a computer, tablet, and/or smart phone accessed by a worker).

In some embodiments, the health monitoring device 100 may comprise one or more power modules 120 incorporated into one or more of the elements of the health monitoring device 100. In some embodiments, the power module(s) 120 may comprise a device and/or system to recharge/trickle charge a battery (e.g., power supply within the health monitoring computer 110) on the health monitoring device (or ear tag) 100. In some embodiments, the power module 110 may comprise an integrated power module 120 configured to be (at least semi) permanently attached to or incorporated into the data collection housing 101. In some embodiments, the power module 120 may comprise a removeable/replaceable module configured to connect to the data collection housing 101 and be in electric communication with the health monitoring computer 110.

In some embodiments, the power module 120 may comprise a charging component 125 or system configured to be exposed to solar rays while attached to an animal (e.g., while in use) to recharge and/or trickle charge at least one or more elements of the health monitoring device 100 (e.g., battery 118). In an embodiment, a solar panel/array 125 of the power module 120 may be exposed on the backside 109 of the data collection housing 101. In an embodiment, a solar panel/array 125 of the power module 120 may be exposed on the frontside 107 of the data collection housing 101. In an embodiment, a solar panel/array 125 of the power module 120 may be exposed on both sides of the data collection housing 101.

In some embodiments, at least a portion of the power module 120 may be incorporated into the attachment body 104, wherein at least a portion of the power module 120 may be positioned on the ear 605 of the animal 603 while the tag 100 is worn by the animal 603. For example, a solar panel/array 125 of the power module 120 may be incorporated into the attachment body 104. In some embodiments, the attachment body 104 may comprise a male portion 104a and a female portion 104b configured to attach to one another through the animal's ear to secure the health monitoring device 100 to the animal's ear 605. In an embodiment the male portion 104a and the female portion 104b are attached via an engagement of a tensioning, engagement, and/or locking system 113 having components incorporated into one or both of the male portion 104a and the female portion 104b of the attachment body. Such system 113 may comprise a screw-type connection system, a spring-loaded-type connection system, a compression/expansion-type connection system, or combinations thereof.

In an embodiment, a solar panel/array 125 of the power module 120 may be incorporated into a male portion 104a of attachment body 104 (e.g., on a portion of the male portion 104a in proximity to a backside of an animal's ear 605 and therefore the solar panel/array 125 is located on the backside of an animal's ear 605).

In an embodiment, a solar panel/array 125 of the power module 120 may be incorporated into a female portion 104b of attachment body 104 (e.g., on a portion of the female portion 104b in proximity to a frontside of an animal's ear 605 and therefore the solar panel/array 125 is located on the frontside of an animal's ear 605).

In an embodiment, a solar panel/array 125 of the power module 120 may be incorporated into a male portion 104a of attachment body 104 (e.g., on a portion of the male portion 104a in proximity to a frontside of an animal's ear 605 and therefore the solar panel/array 125 is located on the frontside of an animal's ear 605).

In an embodiment, a solar panel/array 125 of the power module 120 may be incorporated into a female portion 104b of attachment body 104 (e.g., on a portion of the female portion 104b in proximity to a backside of an animal's ear 605 and therefore the solar panel/array 125 is located on the backside of an animal's ear 605).

In an embodiment, a solar panel/array 125 of the power module 120 may be incorporated into a male portion 104a and a female portion 104b of attachment body 104 (e.g., portions of the solar panel/array 125 are located on both the frontside and backside of an animal's ear 605).

In some embodiments, at least a portion of the power module 120 may be incorporated into the attachment body 104, wherein at least a portion of the power module 120 may be positioned on the ear 605 of the animal 603 while the tag 100 is worn by the animal 603. For example, a solar panel/array 125 of the power module 120 may be incorporated into the attachment body 104. In some embodiments, the attachment body 104 may comprise a male portion 104a and a female portion 104b configured to attach to one another through the animal's ear to secure the health monitoring device 100 to the animal's ear 605. In an embodiment the male portion 104a and the female portion 104b are attached via an engagement of a tensioning, engagement, and/or locking system 113 having components incorporated into one or both of the male portion 104a and the female portion 104b of the attachment body. Such system 113 may comprise a screw-type connection system, a spring-loaded-type connection system, a compression/expansion-type connection system, or combinations thereof. In some embodiments, the male portion 104a may comprise a cavity configured to allow engagement with a prong, for example, for placement on the animal's ear. In some embodiments, the system 113 may be configured to provide a route of electrical communication between the male portion 104a and the female portion 104b of the attachment body and/or a route of signal communication between the male portion 104a and the female portion 104b of the attachment body when the male portion 104a and the female portion 104b are engaged. For example, in various embodiments, the system 113 may comprise one or more pairs of contacts configured to provide the electrical and/or signal communication. In various embodiments, the system 113 may provide a route of electrical and/or signal communication between a component associated with the male portion 104a and a component associated with the female portion 104b, for example, electrical and/or signal communication between the solar panel/array 125 and one or more of the health monitoring computer 110, the power modules 120, and the battery 118.

In some embodiments, the health monitoring device 100 may comprise an indicator that is electrically connected to the power module 120 to indicate when the power module 120 is operational and supplying power to the health monitoring device 100. For example, a visual or audible indicator may be activated whenever successful connection is made with the power module 120 and the health monitoring device 100.

In some embodiments, the power module 120 may be configured to wirelessly communicate information (e.g., via the wireless communication module of the health monitoring computer 110) such as operational status, battery status, health of the device, etc.

In some embodiments, the power module 120 may comprise a quick charge module configured to temporarily attach to the health monitoring device 100 (e.g., to the housing 101) to recharge one or more elements of the health monitoring device 100. In other embodiments, the quick charge module may be incorporated into the health monitoring device 100 and may be configured to connect to a quick charge source to receive power and recharge one or more elements of the health monitoring device 100.

It should be understood that body temperature measurements in livestock can indicate useful information related to the health of the animal illnesses, disease, distress, and hormone levels.

In some embodiments, the on/off switch 102 may be configured to reduce the risk of the animal deactivating the health monitoring device. In an embodiment where in the switch 102 is a depression switch, during use, the worker can determine whether the system is active by depressing the switch 102.

The rotational feature 103 of the health monitoring device 100 and/or the material of the temperature probe 124 (e.g., capable of changing hardness) may allow for stabilization and comfort of the temperature probe 124 in the animal ear 605.

In one embodiment, it is contemplated that the health monitoring device 100 can function independently by way of the notification device 116 when a user set parameter is breached. For example, if the animal's temperature increases to a certain value and/or remains at or above a certain value for a period of time, as predetermined and set by the user, the notification device 116 (e.g., a light) will signal to the user (via illuminating) that such a parameter has been met, allowing for quick visual identification of ill livestock.

Figure 4C:
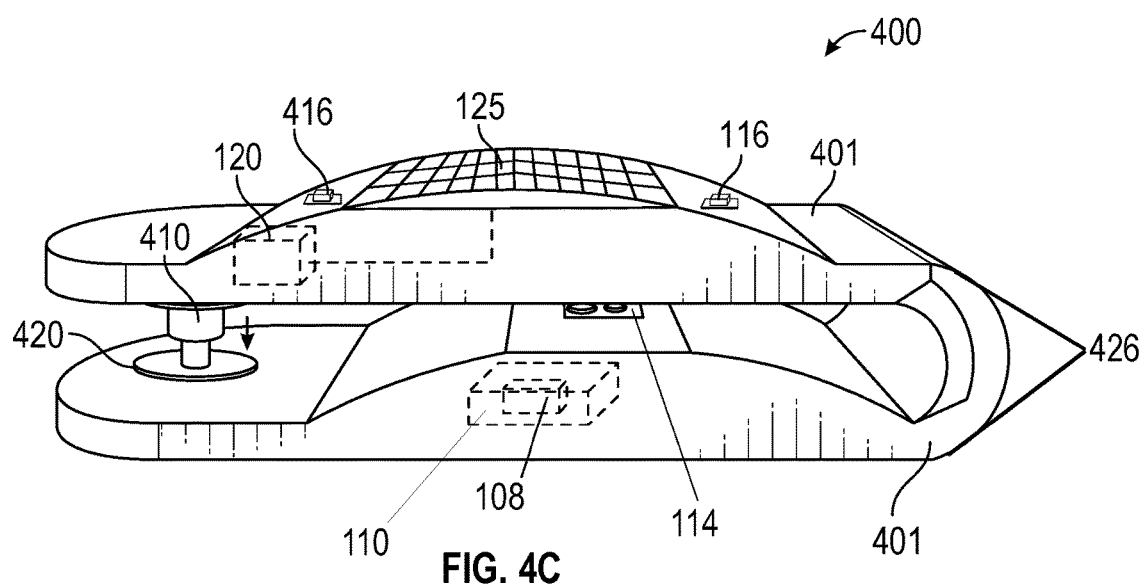
FIG. 4C illustrates a side perspective view of a heath monitoring device according to an embodiment of the disclosure.
Figure 4D:
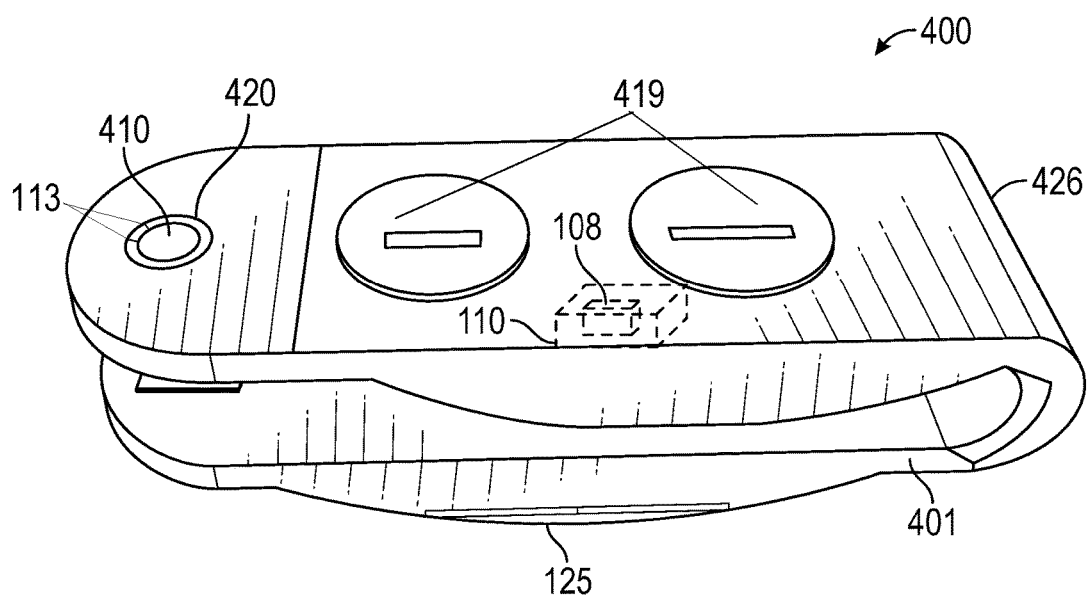
FIG. 4D illustrates a back perspective view of a heath monitoring device according to an embodiment of the disclosure.
Figure 4E:
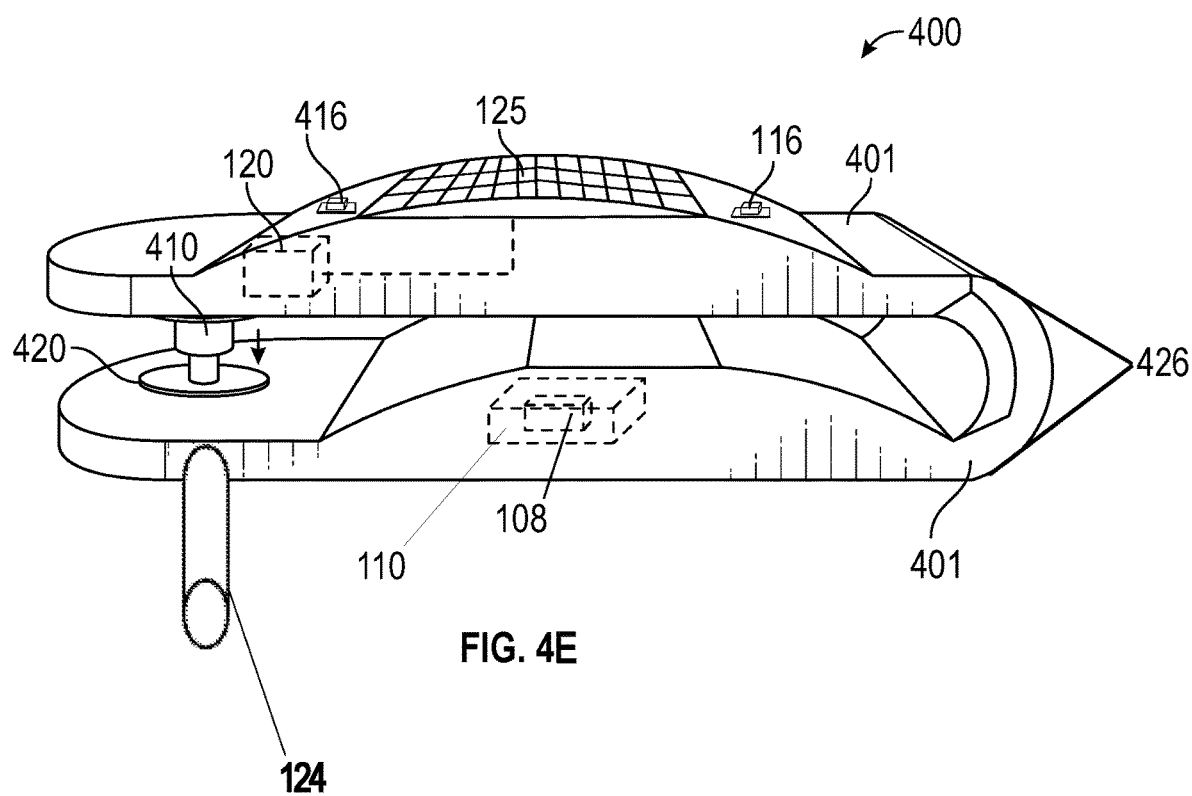
FIG. 4E illustrates a side perspective view of a heath monitoring device according to an embodiment of the disclosure.

In FIGS. 4C, 4D, and 4E, other embodiments of a health monitoring device 400 are shown. In the embodiment of FIGS. 4C and 4D, the health monitoring device 400 generally comprises a data collection housing 401. In the embodiment of FIGS. 4C and 4D, the data collection housing 401 may comprise an on/off switch 102 (e.g., a depression switch) (not shown), which may be incorporated within the housing 401. Also, the data collection housing 401 comprise a temperature sensor 114, which may also be incorporated within the housing 401 such that, when the health monitoring device 400 is positioned with respect to an animal, the temperature sensor 114 will be disposed proximate and/or adjacent to a portion of the animal (e.g., the animal's ear). Additionally or alternatively, as shown in FIG. 4E, in some embodiments the temperature monitoring component may comprise temperature probe 124, for example, such that the temperature monitoring component may be disposed, for example, within the animal's ear canal, as similarly disclosed with respect to one or more other embodiments disclosed herein. Also, in some embodiments, the data collection housing 401 may comprise a notification device 116. As previously disclosed, in various embodiments, the notification device 116 may comprise a visual alert, an audible alert, and/or a wireless alert that is communicated to another device. For example, the notification device 116 may comprise a light that can be visually seen by a worker, an audible speaker, and/or a transmitter configured to provide notification to a remote device (for example, as depicted in FIG. 8).

In the embodiments of FIGS. 4C, 4D, and 4E, the housing 401 generally comprises an integral "clip" configuration 426. For example, in the embodiments of FIGS. 4C and 4D, both a male attachment component 410 and a female attachment component 420 are incorporated and/or integrated into the housing 401. Generally, the male attachment component 410 and the female attachment component 420 are configured to be engaged with one another, for example, so as to secure a first terminal end of the housing 401 with respect to a second terminal end of the housing 401. In some embodiments, the male attachment component 410 may be configured such that upon engagement with the female attachment component 420, the male attachment component 410 would need to be destroyed in order to remove the health monitoring device from the animal's ear. Such embodiments may be effective to prevent reuse of the health monitoring device 400. In various embodiments, the male attachment component 410 and the female attachment component 420 are configured to attach to one another through the animal's ear to secure the health monitoring device 400 to the animal's ear 605. In an embodiment the male attachment component 410 and the female attachment component 420 are attached via an engagement of a tensioning, engagement, and/or locking system 113 having components incorporated into one or both of the male attachment component 410 and the female attachment component 420 of the attachment body. Such system 113 may comprise a screw-type connection system, a spring-loaded-type connection system, a compression/expansion-type connection system, or combinations thereof.

As also similarly disclosed with respect to FIGS. 3, 4A and 4B, in some embodiments the health monitoring computer 110 may be disposed within housing 401 and may comprise software, hardware, and power supply configured to determine if a temperature threshold is reached and/or to activate the notification device 116. The health monitoring computer 110 may receive information from the temperature sensor 114 or temperature probe 124 via a suitable route of communication. The computer system may also comprise a wireless communication module 108 configured to wirelessly communication information to and/or from a remote device (for example, a computer, tablet, and/or smart phone accessed by a worker).

In some embodiments, the health monitoring device 400 may comprise one or more power modules 120 incorporated into one or more of the elements of the health monitoring device 400. In some embodiments, the power module(s) 120 may comprise a device and/or system to recharge/trickle charge a battery (e.g., power supply within the health monitoring computer 110) on the health monitoring device 400 (or ear tag). In some embodiments, the power module 120 may comprise an integrated power module 120 configured to be (at least semi) permanently attached to or incorporated into the data collection housing 401. In some embodiments, the power module 120 may comprise a removeable/replaceable module configured to connect to the data collection housing 401 and be in electric communication with the health monitoring computer 110.

As also similarly disclosed with respect to FIGS. 3, 4A, and 4B, in some embodiments, the power module 120 may comprise a charging component 125 or system configured to be exposed to solar rays while attached to an animal (e.g., while in use) to recharge and/or trickle charge at least one or more elements of the health monitoring device 400 (e.g., battery 118 secured via battery cover 419). In an embodiment, a solar panel/array 125 of the power module 120 may be exposed on one or both sides of the data collection housing 401.

In an embodiment, a solar panel/array 125 of the power module 120 may be incorporated into the data collection housing 401 near the male attachment component 410, near the female attachment component 420, or both.

In some embodiments, the health monitoring device 400 may comprise an indicator 416 that is electrically connected to the power module 120 to indicate when the power module 120 is operational and supplying power to the health monitoring device 100. For example, a visual or audible indicator may be activated whenever successful connection is made with the power module 120 and the health monitoring device 400.

In some embodiments, the power module 120 may be configured to wirelessly communicate information (e.g., via the wireless communication module of the health monitoring computer 110) such as operational status, battery status, health of the device, etc.

Figure 5:
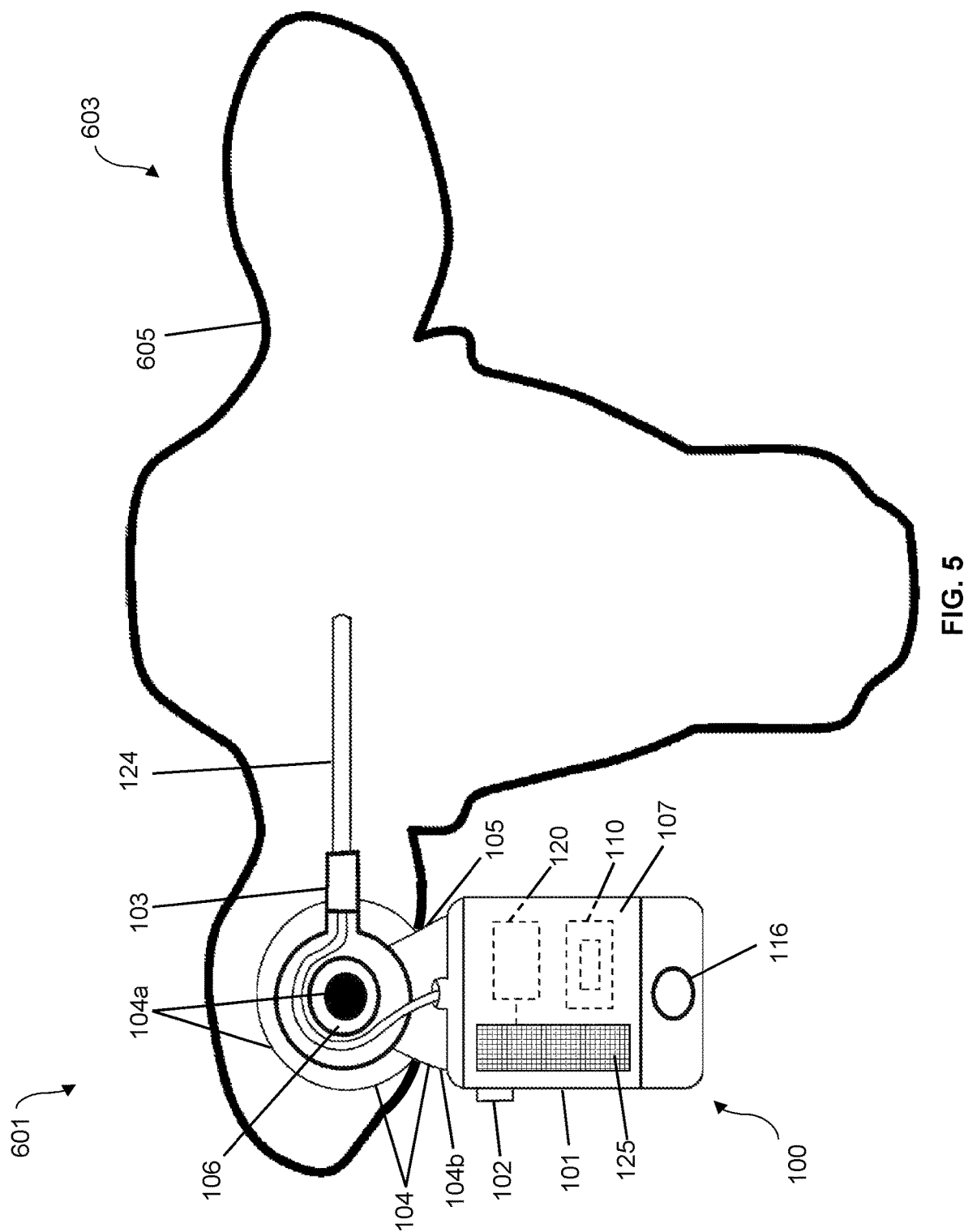
FIG. 5 illustrates a method for monitoring the health of livestock according to an embodiment of the disclosure.

In an embodiment, as shown in FIG. 5, a notification system is disclosed herein wherein a temperature probe 124 is secured within the ear 605 of the animal 603 and provides notification, for example via a light 116, when a threshold temperature 920 reading and/or a duration of time 925 the threshold temperature 920 has been measured is reached. Thus, the health monitoring device 100 is configured to provide notification 930 when the animal 603 falls outside a determined temperature range 920 and/or for a determined duration 925. The notification 930 could be via a light, audible noise, and/or a wireless transmission, as discussed in the below disclosure.

Figure 6:
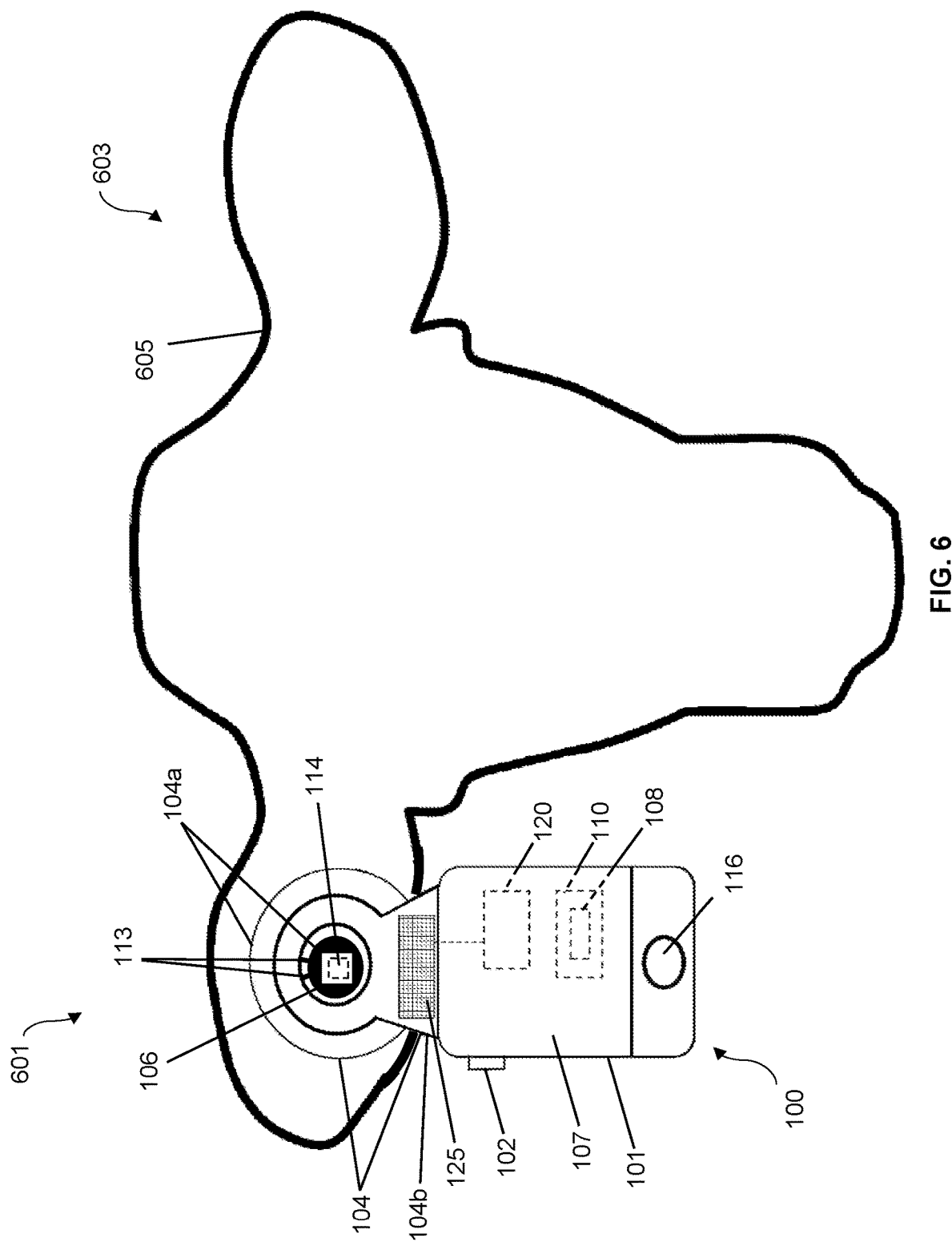
FIG. 6 illustrates a method for monitoring the health of livestock according to an embodiment of the disclosure.

In an embodiment, as shown in FIG. 6, a notification system is disclosed herein wherein a temperature sensor 114 is secured in proximity with the ear 605 of the animal 603 and provides notification, for example via a light, when a threshold temperature 920 reading and/or a duration of time 925 the threshold temperature 920 has been measured is reached. Thus, the health monitoring device 100 is configured to provide notification 930 when the animal 603 falls outside a determined temperature range 920 and/or for a determined duration 925. The notification 930 could be via a light, audible noise, and/or a wireless transmission, as discussed in the below disclosure.

Figure 7A:
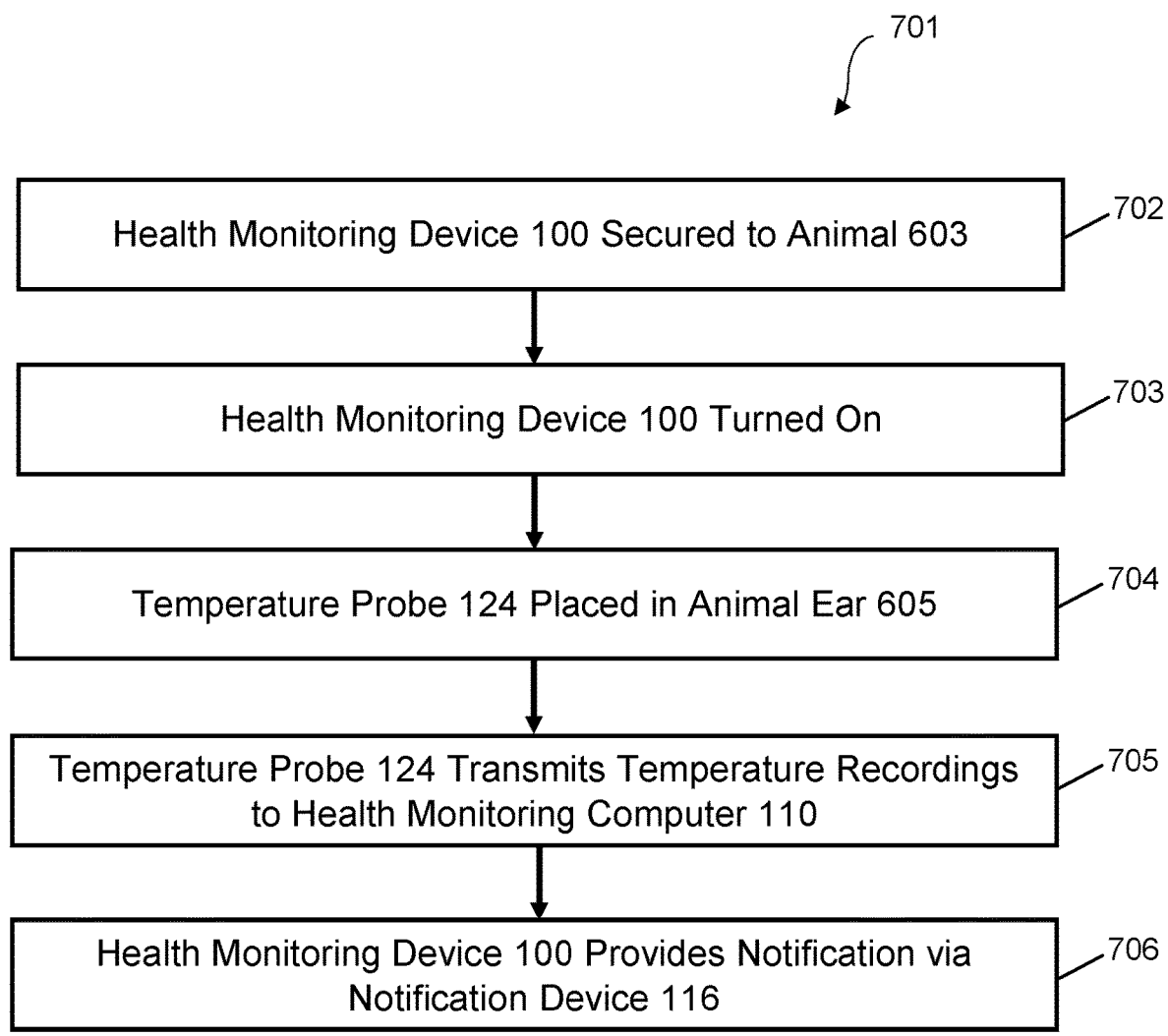
FIG. 7A illustrates a method for monitoring the health of livestock according to an embodiment of the disclosure.

In FIG. 7A, a flowchart 701 depicts an embodiment of a method for monitoring the health of livestock using the elements described in the system 100 shown in FIGS. 1 and 2. At step 702, the heath monitoring device 100 may be secured to the animal's ear 605 via the attachment body 104. At step 703, the health monitoring device 100 may be turned on by the on/off switch 102. At step 704, a temperature probe 124 of the appropriate length is placed in communication with an animal's ear 605. At step 705, the temperature probe 124 may be configured to transmit temperature recordings to the health monitoring computer 110 within the data collection housing 101 via the wire 105. At step 706, the health monitoring device 100 monitors the animal's body temperature and provides a notification related to the data collected by the health monitoring device 100. For example, the notification may comprise current temperature, and/or the notification may comprise an alert (e.g., via notification device 116) that a threshold and or a duration has been reached, possibly indicating an issue.

Figure 7B:
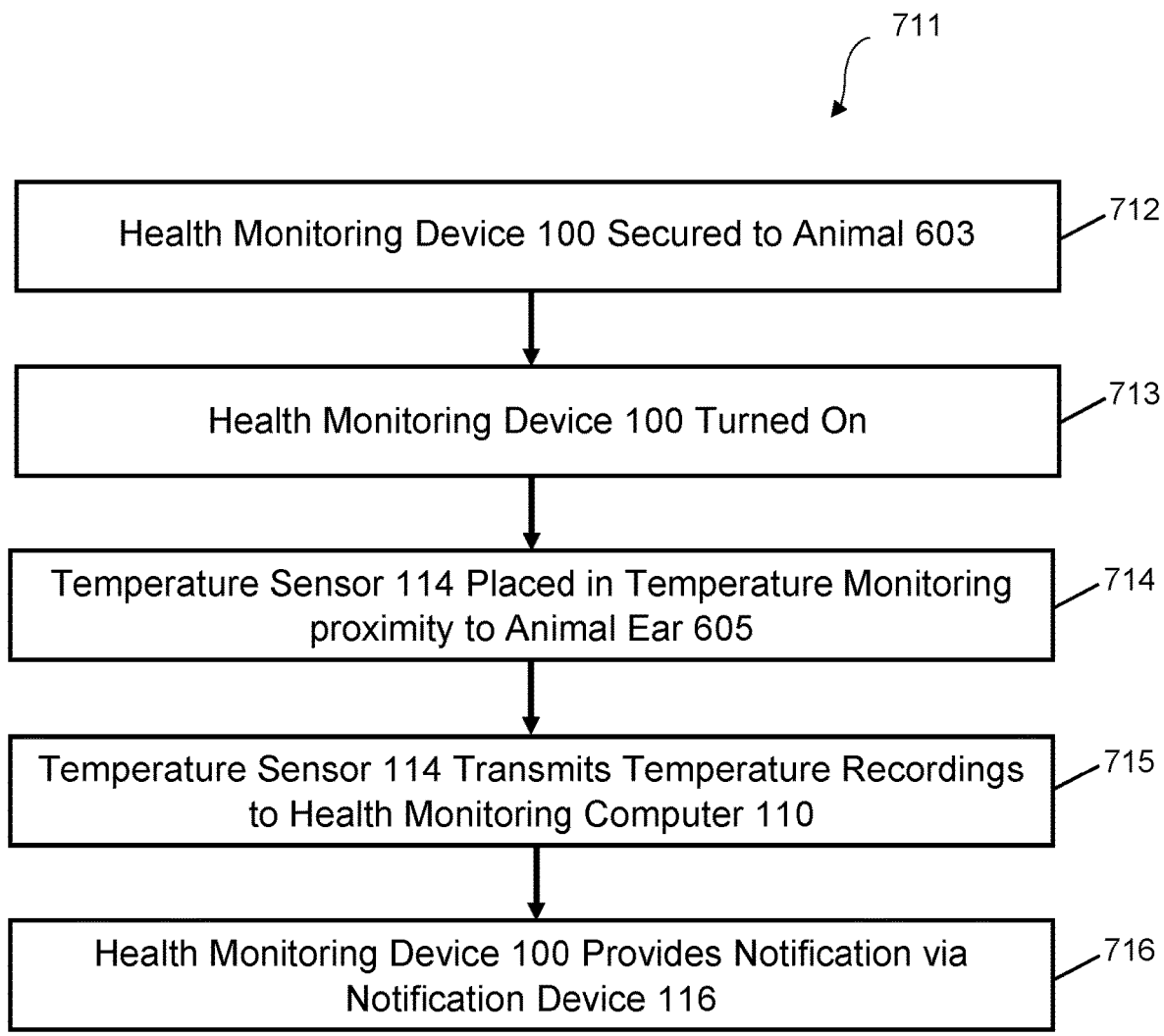
FIG. 7B illustrates a method for monitoring the health of livestock according to an embodiment of the disclosure.

In FIG. 7B, a flowchart 711 depicts an embodiment of a method for monitoring the health of livestock using the elements described in the system 100 shown in FIGS. 3 and 4. At step 712, the heath monitoring device 100 may be secured to the animal's ear 605 via the attachment body 104. At step 713, the health monitoring device 100 may be turned on by the on/off switch 102. At step 714, a temperature sensor 114 is located in a temperature monitoring proximity of an animal's ear 605. At step 715, the temperature sensor 114 may be configured to transmit temperature recordings to the health monitoring computer 110 within the data collection housing 101. At step 716, the health monitoring device 100 monitors the animal's body temperature and provides a notification related to the data collected by the health monitoring device 100. For example, the notification may comprise current temperature, and/or the notification may comprise an alert (e.g., via notification device 116) that a threshold and or a duration has been reached, possibly indicating an issue.

Referring now to FIG. 8, a communication system 801 is shown in accordance with an embodiment of the disclosure. The system 801 may include one or more of the features of the system 801 described above, wherein a health monitoring device 100 may comprise a transmission system 108 (e.g., a wireless communication module) having a transmitter configured to communicate wirelessly to a cloud service 803 and/or database 805 and/or an external computing device 807 such as a smart phone, tablet, computer, server, personal computer, or combinations thereof.

In an embodiment, during use, the system 801 allows the monitoring of multiple animals simultaneously and reduces the chances of human error. For example, the system 801 may comprise a plurality of health monitoring devices 100 each comprising a transmission system 108 configured to send information to the cloud service 803, database 805, and/or external computing device 807 (which may comprise a device monitored by a user). The external computing device 807 could receive information from the plurality of health monitoring devices 100 and may provide notification when the system 801 (described above) is triggered, which in turn allows a worker to conduct visual inspection of the animal(s).

Figure 9:
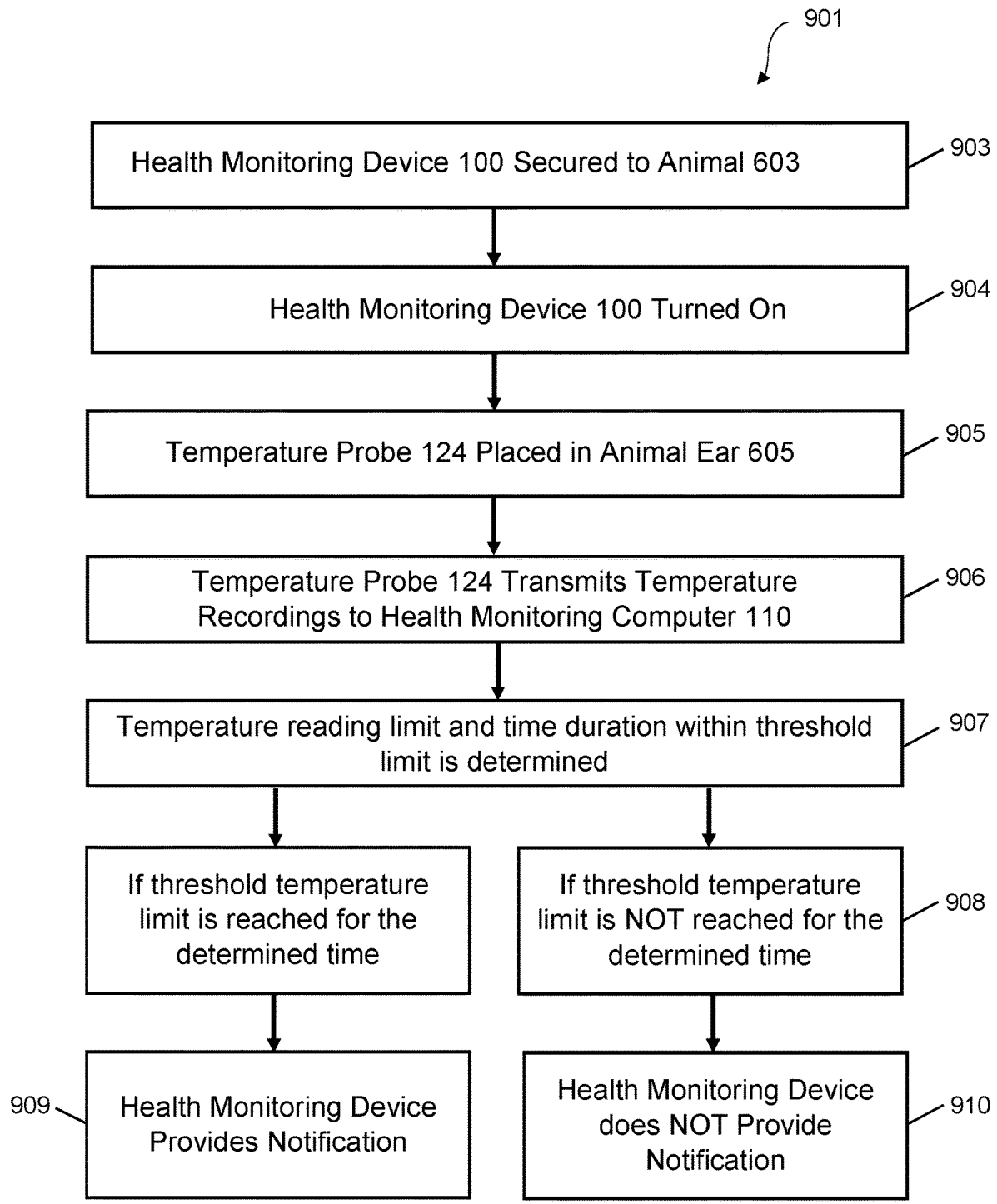
FIG. 9 illustrates a method for monitoring the health of livestock according to an embodiment of the disclosure.

Referring now to FIG. 9, a flowchart 901 depicting a method of use is shown. At step 903 a health monitoring device 100 may be secured to an animal 603 to be monitored. At step 904, the health monitoring device 100 may be activated (or turned on). At step 905, a temperature sensor 114 (or probe 124) of the health monitoring device may be placed in proximity to the ear 605 of the animal 603 so that, at step 906, the temperature sensor 114 (or probe 124) may measure the animal's temperature 910. These steps may be achieved via one or more of the devices discussed above. At step 907, the temperature 910 measured by the temperature sensor 114 (or probe 124) may be communicated and/or transferred to the health monitoring computer 110 via one or more communicators, transmitters, connections (e.g., wire 105), or combinations thereof.

In some embodiments, at step 908, a determination as to whether a temperature threshold 920 which was selected is reached and/or exceeded for a selected time duration 925. One or more computing devices may be used to record and monitor an animal's temperature. In an embodiment, the health monitoring device 100 records and determines whether the animal's temperature remains above the threshold 920 for the selected duration of time 925. If so, at step 909 the health monitoring device 100 provides notice 930. The notice may be in the form of a visual or audible alert, or may be a communication for receipt by an external computing device 807. Further, one or more computers monitoring the animals could provide visual or audible notification via a display. In the alternative, at step 911, if the threshold temperature 920 does not last the selected duration of time 925, the temperature readings are recorded but the health monitoring device 100 does not an alert.

The particular embodiments disclosed above are illustrative only, as the embodiments may be modified and practiced in different but equivalent manners apparent to those skilled in the art having the benefit of the teachings herein. It is therefore evident that the particular embodiments disclosed above may be altered or modified, and all such variations are considered within the scope and spirit of the application. Accordingly, the protection sought herein is as set forth in the description. Although the present embodiments are shown above, they are not limited to just these embodiments, but are amenable to various changes and modifications without departing from the spirit thereof.

What is claimed is:

1. An animal wellness notification system, comprising:
   an attachment body configured to securely engage with an animal's ear;
   a temperature monitoring component;
   a housing secured to the attachment body;
   a power module electrically connected to and configured to provide power to at least one other component of the animal wellness notification system;
   a charging component;
   a computer disposed within the housing; and
   a notification device in data communication with the computer, wherein the notification device is configured to provide notice,
   wherein the computer is configured to:
      receive a selection of a temperature threshold and a time duration for the temperature threshold;
      monitor an animal's temperature;
      determine whether the animal's temperature remains above the temperature threshold for the time duration; and
      cause the notification device to provide the notice upon the animal's temperature exceeding the temperature threshold for the time duration.

2. The system of claim 1, wherein the attachment body comprises a male attachment component and a female attachment component.

3. The system of claim 2, wherein the male attachment component and the female attachment component are both integrated into the housing.

4. The system of claim 3, wherein an engagement of the male attachment component and the female attachment component secures the attachment body to the animal's ear and wherein the attachment body cannot be re-secured to the animal's ear subsequent to removal from the animal's ear.

5. The system of claim 2, wherein the temperature monitoring component is integrated into the male attachment component, the female attachment component, the housing, or combinations thereof.

6. The system of claim 1, wherein the charging component utilizes solar energy to provide electrical energy to the power module.

7. The system of claim 1, the notification device having a transmitter configured to wirelessly communicate with an external computing device.

8. An animal wellness notification system, comprising:
a temperature monitoring component configured to generate temperature data;
a notification device, wherein the animal wellness notification system is configured to:
receive a selection of a temperature threshold and a time duration for the temperature threshold;
record an animal's temperature for the time duration;
determine whether the animal's temperature remains above the temperature threshold for the time duration; and
cause the notification device to provide notice, after the time duration, if the temperature data indicates that the animal's temperature exceeds the temperature threshold for the time duration;
a power module electrically connected to at least one of the temperature monitoring component and the notification device, and configured to provide power to at least one other element of the animal wellness notification system; and
a charging component.

9. The system of claim 8, further comprising:
an attachment body configured to securely engage with an animal's ear;
wherein the temperature monitoring component comprises the attachment body.

10. The system of claim 9, further comprising a housing secured to the attachment body.

11. The system of claim 10, further comprising a computer disposed within the housing and operably associated with the temperature monitoring component.

12. The system of claim 10, wherein the attachment body comprises a male attachment component and a female attachment component.

13. The system of claim 12, wherein the male attachment component and the female attachment component are both integrated into the housing.

14. The system of claim 12, wherein the temperature monitoring component is integrated into the male attachment component, the female attachment component, the housing, or combinations thereof.

15. The system of claim 8, wherein the charging component utilizes solar energy to provide electrical energy to the power module.

16. The system of claim 8, wherein system further comprises:
an external computing device; and
a transmitter configured to wirelessly communicate the temperature data with the external computing device, wherein the external computing device is configured to determine if the temperature data indicates that the animal's temperature exceeds the selected temperature threshold for the selected duration of time.

17. The system of claim 14, wherein an engagement of the male attachment component and the female attachment component secures the attachment body to the animal's ear and wherein the attachment body cannot be re-secured to the animal's ear subsequent to removal from the animal's ear.

18. A method of using an animal wellness notification system to determine the wellness of an animal, comprising:
attaching an animal wellness notification system component to an animal's ear, wherein the animal wellness notification system component comprises a temperature monitoring component;
providing power to the animal wellness notification system via a power module, wherein the power module comprises a rechargeable power source;
a charging component; and
selecting, via a computer associated with the animal wellness notification system, a temperature threshold and a time duration for the temperature threshold, wherein the computer is configured to:
record an animal's temperature for the time duration;
determine whether the animal's temperature remains above the temperature threshold for the time duration; and
cause a notification device associated with the animal wellness notification system to provide notice, after the time duration, if temperature data from the temperature monitoring component indicates that the animal's temperature exceeds the temperature threshold for the time duration.

19. The method of claim 18, wherein the animal wellness notification system component is secured to the animal's ear via an engagement of a male attachment component and a female attachment component and wherein the temperature monitoring component comprises the male attachment component, the female attachment component, a housing, or combinations thereof.

20. The method of claim 18, wherein the charging component utilizes solar energy to recharge the power module.

* * * * *